United States Patent
Horiuchi

[19]

[11] Patent Number: 6,137,858
[45] Date of Patent: *Oct. 24, 2000

[54] RADIATION TOMOGRAPHY METHOD AND APPARATUS

[76] Inventor: Tetsuya Horiuchi, 7-127, Asahigaoka 4-chome, Hino-shi, Tokyo 191-8503, Japan

[*] Notice: This patent is subject to a terminal disclaimer.

[21] Appl. No.: 09/146,692

[22] Filed: Sep. 3, 1998

[51] Int. Cl.[7] ........................................... A61B 6/00
[52] U.S. Cl. .............................. 378/19; 378/336.1; 378/4
[58] Field of Search .................................... 378/19, 336.1, 378/4; 250/336.1

[56] References Cited

U.S. PATENT DOCUMENTS

| | | |
|---|---|---|
| 4,403,289 | 9/1983 | Lux et al. . |
| 5,126,938 | 6/1992 | Oda . |
| 5,430,784 | 7/1995 | Ribbner . |
| 5,570,403 | 10/1996 | Yamazaki . |
| 5,991,356 | 11/1999 | Horiuchi et al. . |

FOREIGN PATENT DOCUMENTS

| | | |
|---|---|---|
| 0662305 | 12/1994 | European Pat. Off. . |
| 19748891 | 6/1998 | Germany . |

OTHER PUBLICATIONS

Yik S. Kwoh et al "A new ct collimator for producing two simultaneous over–lapping slices from one scan" IEEE Trans. Biomedical Engin. vol. bme–28, No. 9, Sep. 1981, pp. 664–668.

*Primary Examiner*—David V. Bruce
*Assistant Examiner*—Pamela R. Hobden

[57] ABSTRACT

A radiation tomography method and apparatus which can image at a time a plurality of tomographic images which differ in slice thickness is implemented. A projection image of a subject projected by a radiation beam 40 having an extent and a thickness is divided in the thickness direction of the radiation beam by detector arrays 240 and 242, and their respective projection data are measured in a plurality of view directions. Then, the tomographic images are produced respectively based on the projection data for each of the divided projection images and the projection data for all of the divided projection images.

14 Claims, 6 Drawing Sheets

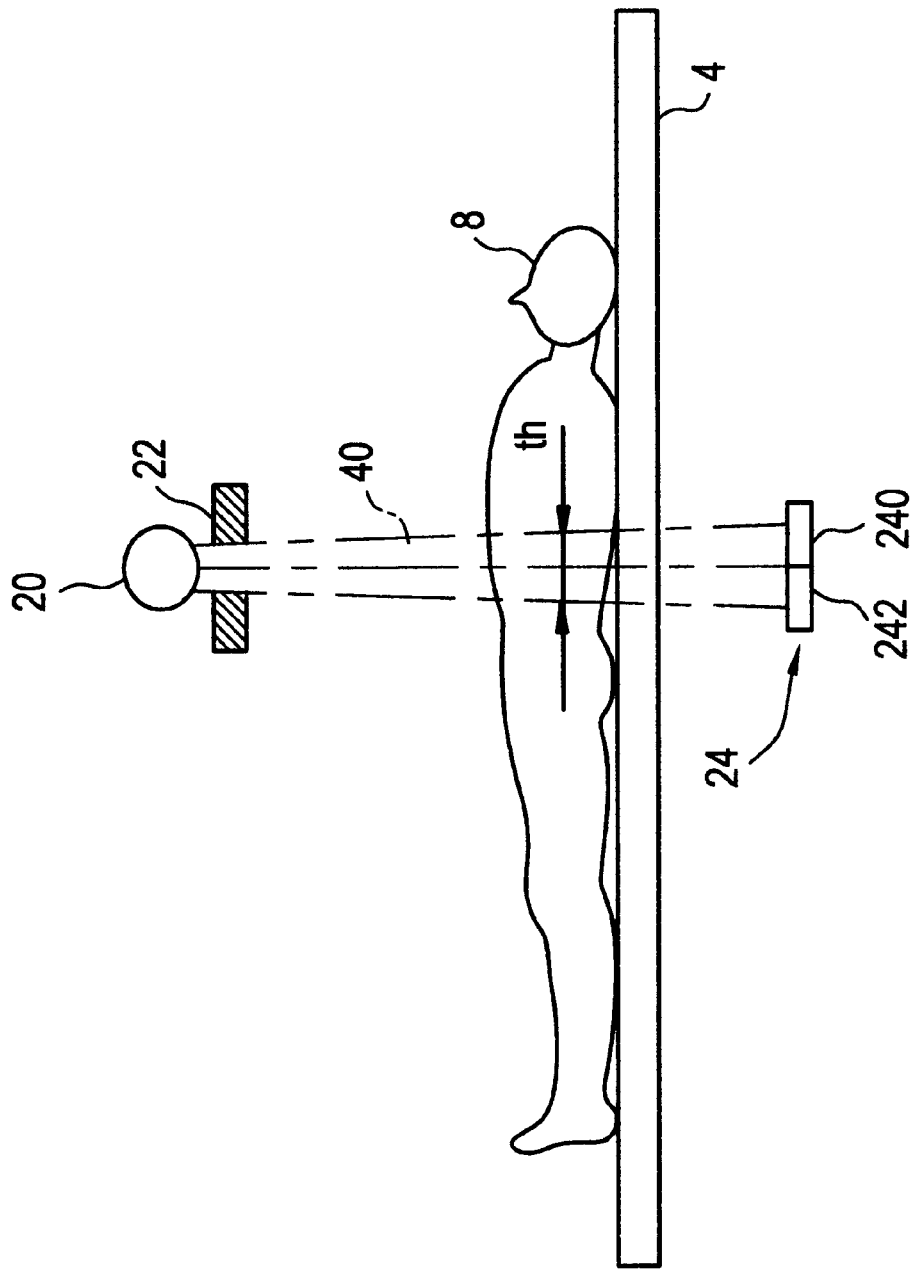

RADIATION TOMOGRAPHY METHOD AND APPARATUS

BACKGROUND OF THE INVENTION

The present invention relates to a radiation tomography method and apparatus, and more particularly, to a radiation tomography method and apparatus which can produce a tomographic image based on a projection image of a subject in a plurality of view directions using a radiation beam having an extent and a thickness.

Radiation tomography apparatuses include the x-ray CT (computed tomography) apparatus, for example. In the x-ray CT apparatus, x-rays are employed as radiation. The apparatus scans a subject by a radiation emission/detection system rotating around the subject to measure x-ray projection data of the subject in a plurality of view directions around the subject, and produces (i.e., reconstructs) a tomographic image based on the projection data.

The radiation emission system has an extent which encompasses the imaging range, and emits an x-ray beam which has a predetermined thickness in the direction orthogonal to the extent. The radiation detection system detects the projection data by a multi-channel detector in which multiple x-ray detectors are arranged in an array in the extent direction of the x-ray beam.

The thickness of the x-ray beam determines the slice thickness for tomography. The slice thickness is set to an appropriate value according to the purpose of tomography. To set the slice thickness, a collimator or the like to regulate the thickness of the x-ray beam is used. Even if radiation other than x-rays, such as γ-rays is employed, the thickness of a radiation beam, i.e., the slice thickness is regulated also by the collimator or the like.

In the case of pulmonary cancer examination, for example, a multi-slice scan with a relatively thick slice is carried out to efficiently and contiguously image the entire lung field with a limited number of slices. In addition, a multi-slice scan with a thin slice is carried out to obtain an image having good detail definition. However, since the number of slices is limited, the multi-slice scan with a thin slice is performed on the slices lying at intervals.

The set slice thickness is maintained throughout the imaging of a sequence of tomographic images. Accordingly, when the multi-slice scanning is performed as described above, a contiguous scan for the entire lung field with a thick slice is first carried out, and then the slice thickness must be reset by the collimator or the like to restart another multi-scan with a thin slice. This procedure is poor in efficiency.

SUMMARY OF THE INVENTION

It is an object of the present invention to implement a radiation tomography method and apparatus which can image at a time a plurality of tomographic images which differ in slice thickness.

In accordance with a first aspect, the present invention provides a radiation tomography method comprising the steps of: with a projection image of a subject projected by a radiation beam having an extent and a thickness divided into divided projection images in the thickness direction of the radiation beam, measuring their respective projection data in a plurality of view directions; and producing tomographic images respectively based on the projection data for each of the divided projection images and the projection data for all of the divided projection images.

In the invention as described regarding the first aspect, the division is preferably unequal division in that a plurality of tomographic images having a significant difference in slice thickness can be obtained.

Moreover, in the invention as described regarding the first aspect, the radiation is preferably x-rays in that practical means for generation, control etc. of x-rays are most widely available.

In accordance with a second aspect, the present invention provides a radiation tomography apparatus comprising: measuring means which, with a projection image of a subject projected by a radiation beam having an extent and a thickness divided into divided projection images in the thickness direction of the radiation beam, measures their respective projection data in a plurality of view directions; and tomographic producing means for producing tomographic images respectively based on the projection data for each of the divided projection images and the projection data for all of the divided projection images.

In the invention as described regarding the second aspect, the measuring means preferably includes dividing means for dividing the projection image of the subject projected by the radiation beam unequally in the thickness direction of the radiation beam in that a plurality of tomographic images having a significant difference in slice thickness can be obtained.

Moreover, in the invention as described regarding the second aspect, the measuring means preferably includes thickness regulating means for regulating the thickness at which the projection image of the subject projected by the radiation beam is divided in the thickness direction of the radiation beam in that the slice thickness of the tomographic image can be regulated.

Furthermore, in the invention as described regarding the second aspect, the radiation is preferably x-rays in that practical means for generation, control etc. of x-rays are most widely available.

In accordance with a third aspect, the present invention provides a radiation tomography apparatus comprising: measuring means for measuring a projection image of a subject projected by a radiation beam having an extent and a thickness, in a plurality of view directions, using a plurality of radiation detectors disposed side by side in the thickness direction of the radiation beam; and tomographic producing means for producing tomographic images respectively based on projection data acquired by each of the plurality of radiation detectors in the measuring means and projection data acquired by all of the plurality of radiation detectors.

In the invention as described regarding the third aspect, the measuring means preferably includes distributing means for distributing the projection image of the subject projected by the radiation beam to the plurality of detectors unequally in the thickness direction of the radiation beam in that a plurality of tomographic images having a significant difference in slice thickness can be obtained.

Moreover, in the invention as described regarding the third aspect, the measuring means preferably includes thickness regulating means for regulating the thickness of the projection image of the subject projected by the radiation beam in that the slice thickness of the tomographic image can be regulated.

Furthermore, in the invention as described regarding the third aspect, the radiation is preferably x-rays in that practical means for generation, control etc. of x-rays are most widely available.

According to the present invention, for the divided projection images of the subject divided in the thickness direction of the radiation beam, their respective projection data are measured to acquire a plurality of series of projection data. Then a tomographic image is produced which has a slice thickness corresponding to the thickness of the radiation beam based on all series of the projection data, and a tomographic image is produced which has a thinner thickness based on one series of the projection data.

Therefore, according to the present invention, a radiation tomography method or apparatus is implemented which can image at a time a plurality of tomographic images which differ in slice thickness, because, with a projection image of a subject projected by a radiation beam having an extent and a thickness divided into divided projection images in the thickness direction of the radiation beam, their respective projection data are measured in a plurality of view directions, and the tomographic images are produced respectively based on the projection data for each of the divided projection images and the projection data for all of the divided projection images.

Further objects and advantages of the present invention will be apparent from the following description of the preferred embodiments of the invention as illustrated in the accompanying drawings.

BRIEF DESCRIPTION OF THE DRAWINGS

FIG. 4 is a schematic view illustrating the configuration of an x-ray emission/detection system in an apparatus in accordance with one embodiment of the present invention.

DETAILED DESCRIPTION OF THE INVENTION

In the following, some embodiments of the present invention will be described in more detail with reference to the accompanying drawings.

Figure 1:
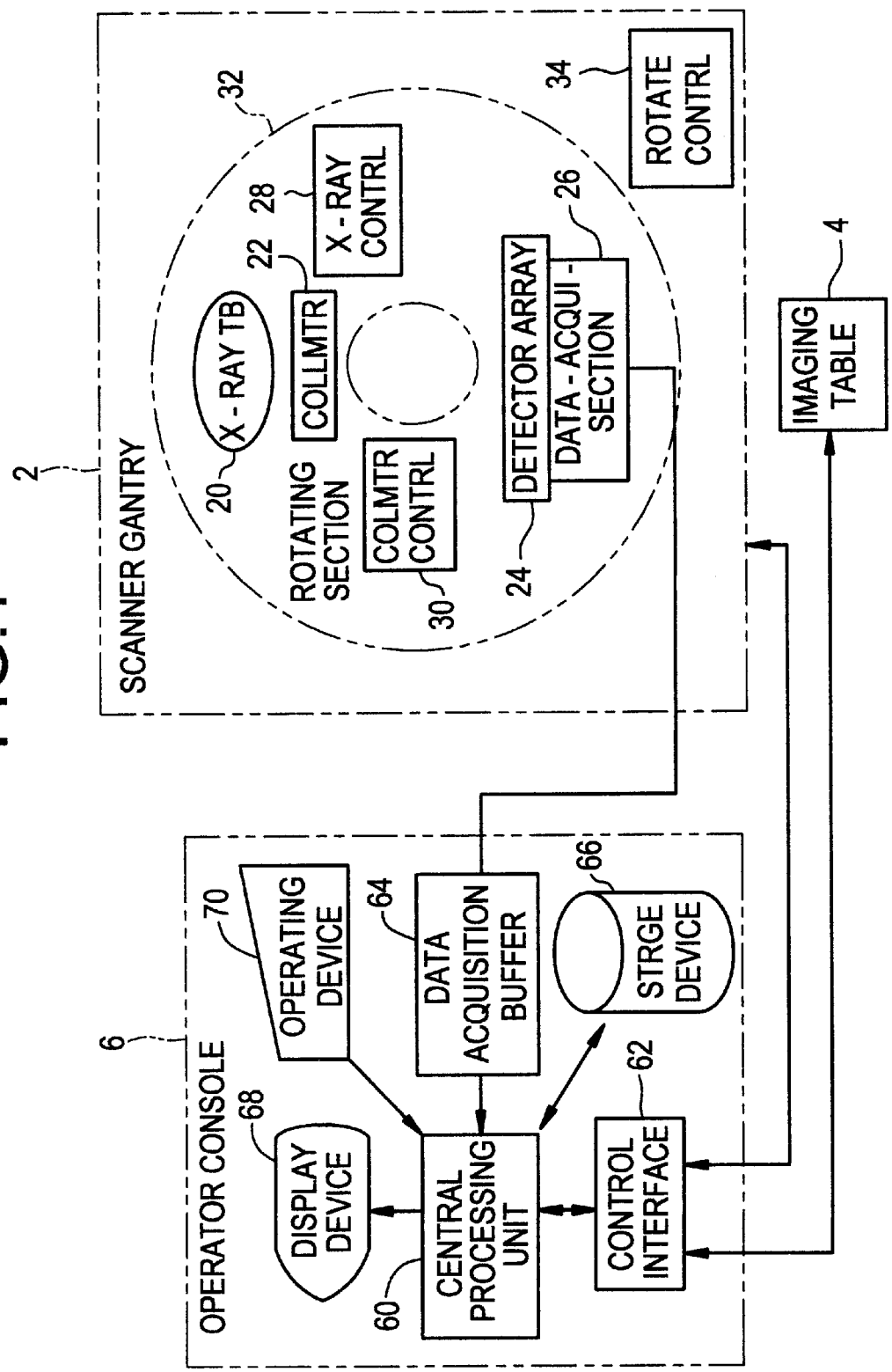
FIG. 1 is a block diagram of an apparatus in accordance with one embodiment of the present invention.

FIG. 1 shows a block diagram of an x-ray CT apparatus. The apparatus is the exemplary implementation of the present invention. Its configuration represents one embodiment of the invention. Its operation represents another embodiment of the invention.

(Configuration)

The configuration of the present apparatus will now be described. As shown in FIG. 1, the apparatus comprises a scanner gantry 2, an imaging table 4 and an operator console 6.

The scanner gantry 2 has an x-ray tube 20 as a radiation source. X-rays (not shown) emanating from the x-ray tube 20 are formed into, for example, a fan-shaped x-ray beam by a collimator 22 and the beam impinges upon a detector array 24.

The detector array 24 has a plurality of x-ray detectors arranged in an array in the extent direction of the fan-shaped x-ray beam. The detailed configuration of the detector array 24 will be described later.

The x-ray tube 20, the collimator 22 and the detector array 24 compose an x-ray emission/detection system. The detailed configuration thereof will be described later. The detector array 24 is connected with a data acquisition section 26. The data acquisition section 26 collects data detected by the individual x-ray detectors in the detector array 24.

Emission of the x-rays from the x-ray tube 20 is governed by an x-ray controller 28. In the drawing, the connection between the x-ray tube 20 and the x-ray controller 28 is not shown.

An x-ray passing aperture of the collimator 22 is regulated by a collimator controller 30. In the drawing, the connection between the collimator 22 and the collimator controller 30 is not shown.

The x-ray tube 20 through the collimator controller 30 are mounted on a rotating section 32 in the scanner gantry 2. Rotation of the rotating section 32 is governed by a rotation controller 34. In the drawing, the connection between the rotating section 32 and the rotation controller 34 is not shown.

The imaging table 4 carries a subject (not shown) into/out of an x-ray irradiation space within the scanner gantry 2. The relationship between the subject and the x-ray irradiation space will be described later.

The operator console 6 has a CPU (central processing unit) 60 which is implemented as a computer, for example. The CPU 60 is connected with a control interface 62. The control interface 62 is connected with the scanner gantry 2 and the imaging table 4.

The CPU 60 controls the scanner gantry 2 and the imaging table 4 via the control interface 62. The data acquisition section 26, the x-ray controller 28, the collimator controller 30 and the rotation controller 34 in the scanner gantry 2 are controlled via the control interface 62. In the drawing, the individual connections between these components and the control interface 62 are not shown.

The CPU 60 is also connected with a data acquisition buffer 64. The data acquisition buffer 64 is connected with the data acquisition section 26 in the scanner gantry 2. The data collected in the data acquisition section 26 is supplied to the data acquisition buffer 64. The data acquisition buffer 64 temporarily stores the supplied data. The CPU 60 is further connected with a storage device 66. The storage device 66 stores various data, reconstructed images, programs and the like.

The CPU 60 is also connected with a display device 68 and a operating device 70. The display device 68 presents a reconstructed image supplied from the CPU 60 and other information. The operating device 70 is manipulated by an operator, and supplies various commands and information to the CPU 60.

Figure 2:
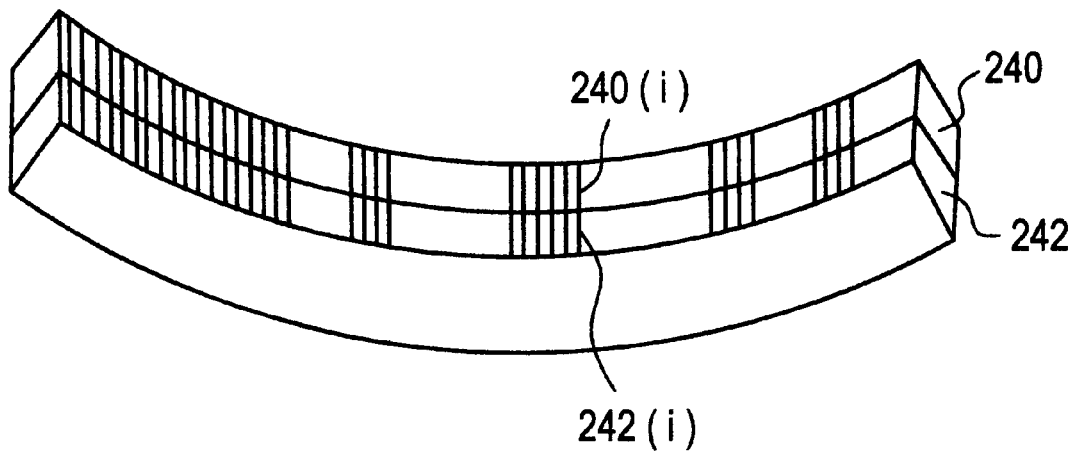
FIG. 2 is a schematic view illustrating the configuration of an x-ray detector array in an apparatus in accordance with one embodiment of the present invention.

FIG. 2 schematically illustrates the configuration of the detector array 24. The detector array 24 has a first row of detector array 240 and a second row of detector array 242 which are combined together. The first and second rows of detector array 240 and 242 are an example of a plurality of radiation detectors in the present invention.

The first row of detector array 240 is constituted as a multi-channel x-ray detector array in which multiple (e.g., 1,000) x-ray detectors 240($i$) are arranged in an arc shape.

The symbol "i" represents a channel number and i=1, . . . , 1,000, for example. Similarly, the second row of detector array 242 is constituted as a multi-channel x-ray detector array in which multiple x-ray detectors 242(*i*) are arranged in an arc shape.

Figure 3A:
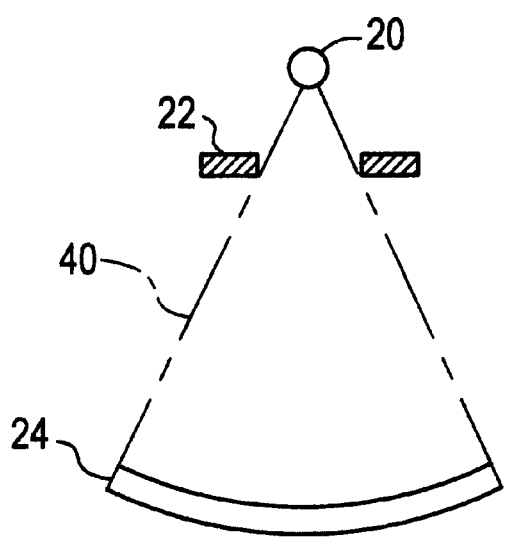
FIGS. 3(A) and 3(B) are schematic views illustrating the configuration of an x-ray emission/detection system in an apparatus in accordance with one embodiment of the present invention.
Figure 3B:
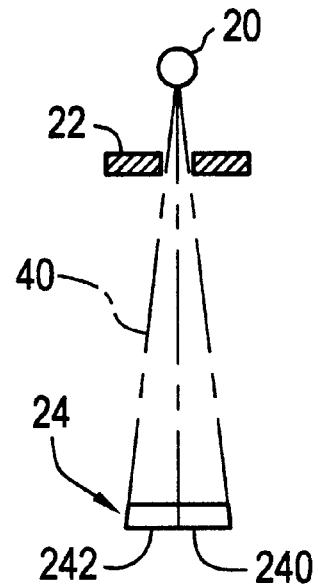

FIGS. 3(A) and 3(B) illustrate the interrelationship among the x-ray tube 20, the collimator 22 and the detector array 24 in the x-ray emission/detection system. FIG. 3(*a*) is a front view and FIG. 3(*b*) is a side view. As shown, x-rays emanating from the x-ray tube 20 are formed into a fan-shaped x-ray beam 40 by the collimator 22 and the beam 40 impinges upon the detector array 24. The fan-shaped x-ray beam 40 is an example of a radiation beam having an extent and a thickness in the present invention.

The subject is inserted with the subject's body axis intersecting the fan plane of the x-ray beam 40. This is illustrated in FIG. 4. As shown, a projection image of a subject 8 sliced by the x-ray beam 40 is projected onto the detector array 24. The thickness of the x-ray beam 40 at the isocenter of the subject 8 is the slice thickness 'th' of the subject 8. The slice thickness 'th' is determined by the x-ray passing aperture of the collimator 22. The collimator 22 is an example of thickness regulating means in the present invention.

The projection image having the thickness of 'th' is projected spanning the first row of detector array 240 and the second row of detector array 242. In other words, the projection image of the subject projected by the x-ray beam 40 is divided into two portions in the thickness direction of the x-ray beam 40 and the divided portions are projected as two projection images. Accordingly, two sets of projection data for the projection images of two adjacent slices juxtaposed in the thickness direction can be obtained respectively from the first row of detector array 240 and the second row of detector array 242. The projection data is an example of projection data in the present invention.

Figure 5:
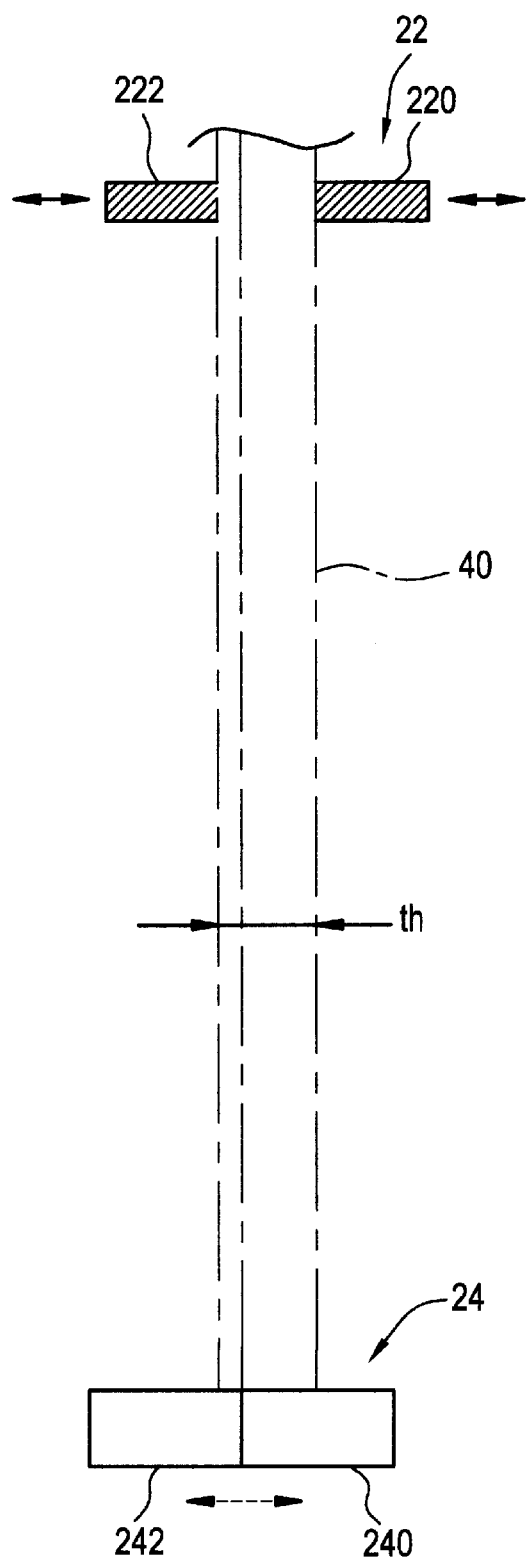
FIG. 5 is a schematic view illustrating the exemplary division of a projection image projected by an x-ray beam in an apparatus in accordance with one embodiment of the present invention.

The dividing ratio of the slice thickness 'th' can be regulated by the collimator 22. For example, as schematically shown in FIG. 5, the slice thickness of the projection image on the second row of detector array 242 can be decreased (i.e., the ratio is decreased) by displacing a collimator block 222 of the collimator 22 in a direction such that the x-ray passing aperture is narrowed. Similarly, the slice thickness of the projection image on the first row of detector array 240 can be increased (i.e., the ratio is increased) by moving another collimator block 220 so as to broaden the x-ray passing aperture. If the ratio is to be set conversely, the moving direction of the collimator blocks 220 and 222 is inverted.

Alternatively, the detector array 24 may be displaced relative to the collimator 22 in the direction of the slice thickness 'th', as indicated by broken line arrow, while fixing the aperture of the collimator 22 at the slice thickness 'th'. This is preferable in that the regulation of the slice thickness and the regulation of the dividing ratio are separated. On the other hand, achieving all of the regulation in the collimator as described before is preferable in that the regulated sections are integrated.

The respective projection data can thus be obtained for the two projection images which are unsymmetrically divided in the slice thickness direction by the first row of detector array 240 and the second row of detector array 242. That is, the projection data for two projection images which differ in slice thickness can be obtained. The two projection images are adjacent in the slice thickness direction. The collimator 22 and the detector array 24 are an example of dividing means in the present invention. They are also an example of distributing means in the present invention. The detector array 24 having the two rows of detector array 240 and 242 is preferable in that the configuration of the distributing means can be simplified.

The x-ray emission/detection system consisting of the x-ray tube 20, the collimator 22 and the detector array 24 rotates (i.e., scans) around the body axis of the subject 8 maintaining their interrelationship. The projection data representing the subject 8 are acquired at a plurality (e.g., 1,000) of view angles per scan rotation. The projection data is acquired by a system consisting of the detector array 24, the data acquisition portion 26 and the data acquisition buffer 64. The projection data acquisition is performed in parallel for the projection images of two adjacent slices. The x-ray tube 20 through the data acquisition portion 26 and the data acquisition buffer 64 are an example of measuring means in the present invention.

Based on the projection data equivalent to those of two slices acquired in the data acquisition buffer 64, the CPU 60 produces a tomographic image, i.e., performs image reconstruction. The CPU 60 is an example of tomographic producing means in the present invention. The image is reconstructed by, for example, filtered back-projection processing the projection data for 1,000 views, for example, obtained from the scanning during one rotation. The image reconstruction operation by the CPU 60 will be described later.

(Operation)

Figure 6:
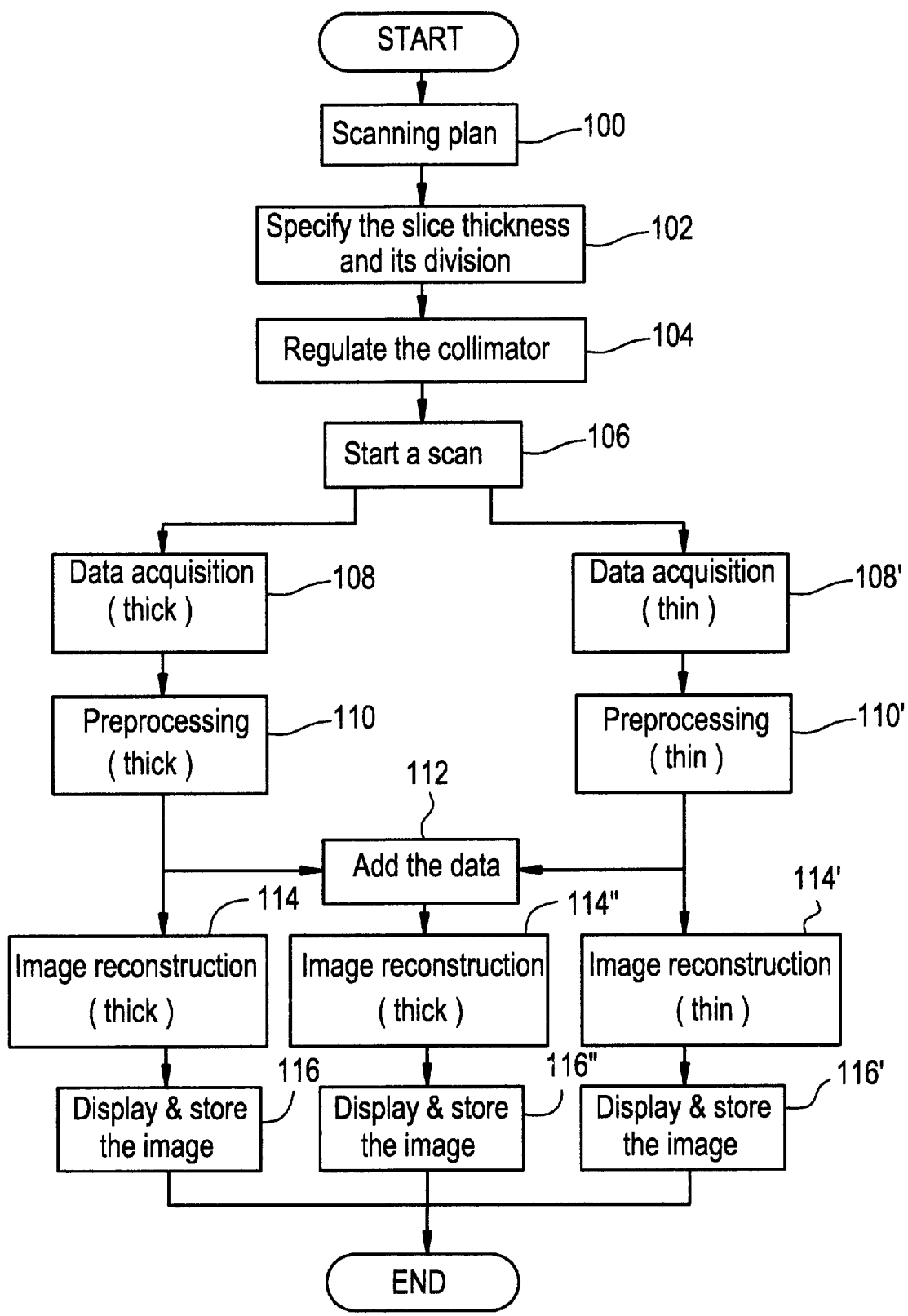
FIG. 6 is a flow chart illustrating the operation of an apparatus in accordance with one embodiment of the present invention.

The operation of the present apparatus will now be described. FIG. 6 shows a flow chart of the operation of the present apparatus. The operation is started based on the commands or the like supplied by the operator to the CPU 60 through the operating device 70.

In Step 100, a scanning plan is first made. The scanning plan is determined by the operator interactively conversing with the CPU 60 via the display device 68 and the operating device 70, for example. The scanning plan specifies an imaging range of the subject 8 and the imaging condition suitable for the imaging range.

As an example, the entire lung field is specified as the imaging range, and the x-ray intensity and other imaging conditions suitable for the lung field imaging are specified. Moreover, assume that the so-called multi-slice scanning technique is employed to produce a plurality of tomographic images while sequentially changing the slice position in order to image the entire lung field.

In Step 102, the slice thickness and its division is then specified. In this example, the slice thickness is set to 10 mm, and its division is set to the dividing ratio 7:3. These settings are also determined by the operator interactively conversing with the CPU 60 via the display device 68 and the operating device 70, for example.

In Step 104, the thickness of the x-ray beam is regulated and distributed. This is done by the CPU 60 controlling the collimator 22 via the collimator controller 30 based on the settings of the slice thickness and its division.

Thus, as shown in FIG. 5 for example, when the thickness of the x-ray beam 'th' is set to 10 mm and it is to be distributed in the ratio 7:3, the thickness of the x-ray beam impinging upon the first row of detector array 240 is 7 mm, and the thickness of the x-ray beam impinging upon the second row of detector array 242 is 3 mm.

In Step 106, a scan is started. Hereafter the CPU 60 controls the scanner gantry 2 and the imaging table 4 to perform the multi-slice scanning. Accordingly, the imaging table 4 is intermittently translated by 10 mm per rotation of the x-ray emission/detection system, and a plurality of contiguous slices each having the thickness of 10 mm are sequentially scanned.

For each scan location, the projection data sets for the 7-mm slice ('thick') and the 3-mm slice ('thin') are acquired in parallel via the two rows of the detector array 240 and 242, respectively, in Steps 108 and 108'.

Figure 7:
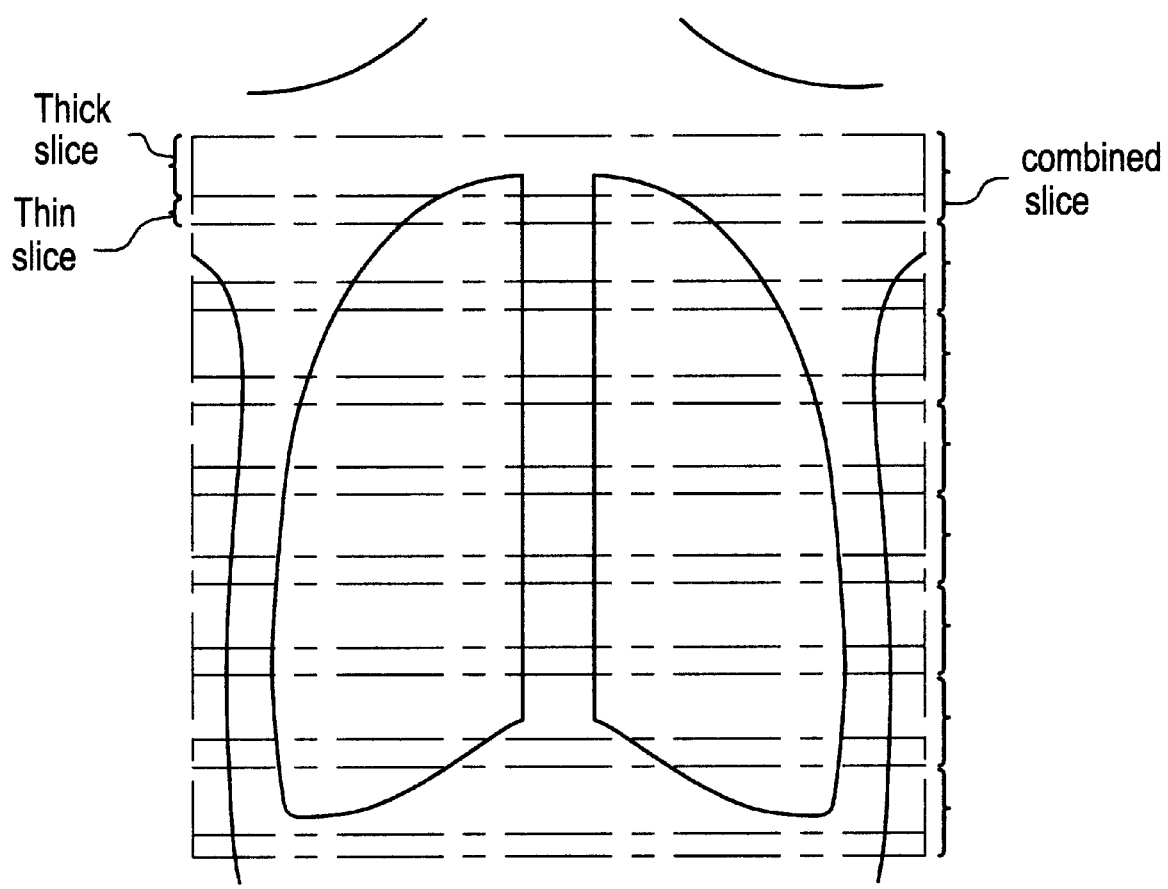
FIG. 7 is a schematic view illustrating an example of a multi-slice scan by an apparatus in accordance with one embodiment of the present invention.

This process is schematically shown in FIG. 7. In the drawing, a thick slice corresponds to the 7-mm slice, a thin slice corresponds to the 3-mm slice and a combined slice corresponds to the 10-mm slice.

Next, in Step 110 and 110', the projection data sets for the two slices are respectively preprocessed for each scan location. The preprocessing includes sensitivity correction, for example, for each row of the detector array corresponding to each slice thickness.

In Step 112, the projection data sets for the two slices are then added for each scan location. The same views in the individual projection data sets are added. This addition generates projection data corresponding to the slice thickness of the combined two slices, i.e., equivalent to projection data for a 10-mm slice.

In Steps 114, 114' and 114", image reconstruction is performed for each scan location. In Step 114, the image reconstruction is performed based on the projection data set for the 7-mm slice. In Step 114', the image reconstruction is performed based on the projection data set for the 3-mm slice. In Step 114", the image reconstruction is performed based on the projection data set for the substantially 10-mm slice. Thus, three tomographic images which differ in slice thickness are obtained for each scan location.

A plurality of tomographic images of the 10-mm slices represent a plurality of slices which are contiguous in the slice thickness direction. A plurality of tomographic images of the 7-mm slices represent a plurality of slices disposed at intervals of 3 mm in the slice thickness direction. A plurality of tomographic images of the 3-mm slices represent a plurality of slices disposed at intervals of 7 mm in the slice thickness direction.

In reconstructing these images, the reconstruction function suitable for each slice thickness is employed. As an example, for the projection data sets of the 10-mm slice and the 7-mm slice, a low frequency band enhancing reconstruction function is used. This provides a tomographic image having good definition in the parenchymal portions of the internal tissue. For the projection data set of the 3-mm slice, a high frequency band enhancing reconstruction function is used. This provides a tomographic image having good definition in the details of the internal tissue.

Consequently, a plurality of tomographic images representing 10-mm slices imaged contiguously over the lung field and a plurality of detailed tomographic images representing 3-mm slices imaged at regular intervals in a sampling-like manner can be obtained at a time in one multi-slice scan. In other words, two kinds of tomographic images which significantly differ in slice thickness can be obtained at a time. The scanning need not be repeated twice with the slice thickness varied as conventionally practiced, which results in excellent efficiency.

Next, in Steps 116, 116' and 116", the image is displayed and stored. The image display is done by the display device 68. The image storage is done by the storage device 66.

By observing the plurality of tomographic images representing the 10-mm slices displayed on the display device 68, one can examine the entire lung field contiguously and exhaustively. Moreover, by observing the plurality of tomographic images representing the 3-mm slices displayed on the display device 68, one can precisely examine the lung field at regular intervals. Furthermore, the tomographic images representing the 7-mm slices can be used for examination if desired.

Although the above description has been made on an exemplary detector array having two rows, the detector array is not limited to have two rows, but may have multiple rows such as three rows or more, and the x-ray beam may be projected over these rows. This is preferable in that tomographic images as many as four or more can be obtained at a time.

Moreover, the case in which the multi-slice scanning technique is employed has been explained, but even when the single-slice scanning technique is employed, a plurality of slices which differ in slice thickness can be imaged at a time, resulting in a great effect on improvement of imaging efficiency.

Furthermore, although x-rays are employed as radiation in the above description, the radiation is not limited to x-rays but may be any other type of radiation such as γ-rays. However, x-rays are currently preferred in that practical means for generating and controlling x-rays are most widely available.

Many widely different embodiments of the invention may be configured without departing from the spirit and the scope of the present invention. It should be understood that the present invention is not limited to the specific embodiments described in the specification, except as defined in the appended claims.

What is claimed is:

1. A radiation tomography method, comprising the steps of:
    scanniing a subject with a scanning beam of radiation in a plurality of slices;
    dividing each slice into at least two unequal parts by dividing the thickness direction of the scanning beam into at least two unequal parts;
    obtaining concurrently and parallely projection data of each of the at least two unequal parts of the scanning beam for each slice; and
    providing tomographic images of each slice based on the projection data of the at least two unequal parts, whereby a plurality of slices with at least one corresponding part of each slice are imaged concurrently.

2. The method of claim 1, wherein said obtaining step is provided by at least two sets of parallely disposed detectors which detect the at least two unequal parts, respectively, of the divided scanning beam.

3. The method of claim 1, wherein the plurality of slices with at least two unequal divided parts of each slice combined are imaged concurrently.

4. The method of claim 1, wherein the plurality of slices with the at least two divided unequal parts of each slice and with one corresponding part of each slice are imaged concurrently.

5. The method of claim 1, wherein said dividing in the thickness direction of said scanning beam is provided by a collimator through which said scanning beam is directed.

6. The method of claim 1, wherein said dividing in the thickness direction of said scanning beam is provided by a detector array.

7. The method of claim 1, wherein said scanning is by X-ray.

8. A radiation tomograph apparatus, comprising:
    means for scanning a subject with a scanning beam of radiation in a plurality of slices;
    means for dividing each slice into at least two unequal parts by dividing the thickness direction of the scanning beam into at least two unequal parts;
    means for obtaining concurrently and parallely projection data of each of the at least two unequal parts of the scanning beam for each slice; and means for providing tomographic images of each slice based on the projection data of the at least two unequal parts, whereby a plurality of slices with at least one corresponding part of each slice are imaged concurrently.

9. The apparatus of claim 8, wherein said means for obtaining comprises at least two sets of parallely disposed detectors which detect the at least two unequal parts, respectively, of the images produced by the divided scanning beam.

10. The apparatus of claim 8, wherein said means for providing tomographic images comprises means for providing images concurrently of the plurality of slices with at least two unequal divided parts of each slice combined.

11. The apparatus of claim 8, wherein said means for providing tomographic images comprises means for providing images concurrently of the plurality of slices with a combination of the at least two unequal parts of each slice and one of the corresponding part of each slice.

12. The apparatus of claim 8, wherein said means for dividing comprises a collimator.

13. The apparatus of claim 8, wherein said means for dividing comprises a detector array.

14. The apparatus of claim 8, wherein said means for scanning comprises means for providing X-rays.

* * * * *